United States Patent [19]

Brahm et al.

[11] Patent Number: 5,580,947
[45] Date of Patent: Dec. 3, 1996

[54] OLEFINICALLY UNSATURATED ISOCYANATES, A METHOD FOR THEIR PRODUCTION AND THEIR USE IN ONE-COMPONENT COATING COMPOSITIONS

[75] Inventors: Martin Brahm, Engelskirchen; Eberhard Arning, Kaarst; Lutz Schmalstieg, Köln; Jürgen Schwindt, Leverkusen; Josef Pedain, Köln, all of Germany

[73] Assignee: Bayer Aktiengesellschaft, Leverkusen, Germany

[21] Appl. No.: 227,160

[22] Filed: Apr. 13, 1994

[30] Foreign Application Priority Data

Apr. 30, 1993 [DE] Germany ................ 43 14 252.4

[51] Int. Cl.$^6$ .................................................. C08G 18/67
[52] U.S. Cl. .................... 528/75; 528/67; 528/80; 528/83; 528/84; 528/85; 526/34; 526/312; 428/423.1; 428/424.2
[58] Field of Search ........................... 528/75, 80, 83, 528/84, 85, 272, 67, 73, 48; 526/34, 312; 428/423.1, 424.2

[56] References Cited

U.S. PATENT DOCUMENTS

| | | | |
|---|---|---|---|
| 3,517,039 | 6/1970 | Wagner et al. | 260/404.5 |
| 4,049,680 | 9/1977 | Blachford | 260/404.5 |
| 4,485,226 | 11/1984 | Noll et al. | 528/45 |
| 4,663,415 | 5/1987 | Grögler et al. | 528/61 |
| 5,319,052 | 6/1994 | Prantl et al. | 528/48 |
| 5,459,214 | 10/1995 | Brahm et al. | 526/301 |

FOREIGN PATENT DOCUMENTS

| | | |
|---|---|---|
| 301345 | 2/1989 | European Pat. Off. . |
| 1484585 | 9/1977 | United Kingdom . |

OTHER PUBLICATIONS

Ullmann, Encyclopädie der technischen Chemie, 4th Edition, vol. 19, pp. 75 et seq, Verlag Chemie Weinheim, Deerfield Beach Florida, Basle, 1980.

Primary Examiner—James J. Seidleck
Assistant Examiner—Duc Truong
Attorney, Agent, or Firm—Joseph C. Gil; Thomas W. Roy

[57] ABSTRACT

A process for the production of olefinically unsaturated isocyanates by reacting a1) isophorone diisocyanate or mixtures of isophorone diisocyanate with a2) other organic polyisocyanates with b1.1) olefinically unsaturated carboxylic acids or mixtures thereof with b1.2) other monobasic or polybasic carboxylic acids, b2.1) olefinically unsaturated alcohols and/or b2.2) other monohydric or polyhydric alcohols, the unsaturated resulting isocyanates and their use as binders for one-component coating compositions which may be cured at room temperature.

13 Claims, No Drawings

OLEFINICALLY UNSATURATED ISOCYANATES, A METHOD FOR THEIR PRODUCTION AND THEIR USE IN ONE-COMPONENT COATING COMPOSITIONS

BACKGROUND OF THE INVENTION

1. Field of the Invention

The present invention relates to a process for the production of olefinically unsaturated isocyanates from isophorone diisocyanate and selected olefinically unsaturated carboxylic acids, to the resulting olefinically unsaturated isocyanates and to their use as binders in one-component coating compositions which may be cured at room temperature.

2. Description of the Prior Art

Coating compositions based on isocyanate functional prepolymers containing urethane groups which are processed as one-component products have long been known (Houben-Weyl, Methoden der organischen Chemie, Volume E20, page 1646, Georg Thieme Verlag 1987). They are produced by the reaction of diisocyanates or modified diisocyanates with higher functional polyols such as polyether or polyester polyols. The relatively high molecular weight structure imparts to these compositions good film-forming properties and good optical properties in the resulting coating. However, the high molecular weight structure also causes a higher viscosity so that the coating compositions can only be used as binders when highly diluted or in combination with a considerable proportion of monomeric diisocyanate. Such high concentrations of monomeric isocyanate are physiologically unacceptable and the use of large quantities of solvents cannot be justified from an environmental point of view.

Based on commercially available materials one must choose between high molecular weight, highly functional products with a high viscosity but advantageous properties or a low molecular weight, low viscosity products with insufficient solvent resistance and insufficient drying properties. A need exists for low viscosity products which possess the properties of high viscosity products.

One-component systems which can be cross-linked oxidatively have been described in addition to isocyanate functional coating materials (Ullmann, Encyclopädie der technischen Chemie, 4th Edition, Volume 19, pages 75 et seq, Verlag Chemie Weinheim, Deerfield Beach Fla., Basle, 1980). These one-component systems also can only be used in dilute solutions as binders for coating materials.

It is an object of the present invention to provide new low viscosity binders for solvent-free or low solvent coating compositions with good properties and rapid chemical drying at room temperature which may be universally used and are physiologically harmless.

This object may be achieved with the process according to the invention described below which results in products which satisfy the above-mentioned requirements for the simultaneous presence of olefinic double bonds, amide groups and optionally urethane groups and isocyanate groups. One essential feature is the balanced ratio of amide groups, isocyanate groups and double bonds which are capable of oxidative cross-linking.

SUMMARY OF THE INVENTION

The invention relates to a process for the production of olefinically unsaturated isocyanates having an isocyanate content of 4 to 20% by weight by reacting a) an isocyanate component having an isocyanate content of 20 to 51% by weight and an (average) functionality of less than 2.5 and containing
  a1) 40 to 100% by weight of isophorone diisocyanate (IPDI) and
  a2) 0 to 60% by weight of one or more other organic polyisocyanates having an isocyanate content of 10 to 60% by weight with b) an olefinically unsaturated reactive component having an average functionality in isocyanate addition reactions of less than 1.5 and an iodine number above 70, and containing
  b1) 1 to 100% by weight of a carboxylic acid component containing
    b1.1) 80 to 100% by weight of one or more monobasic, olefinically unsaturated carboxylic acids having 10 to 22 carbon atoms per molecule and
    b1.2) 0 to 20% by weight of one or more other monobasic or polybasic carboxylic acids having a molecular weight of 46 to 350 and
  b2) 0 to 99% by weight of an alcohol component containing
    b2.1) 0 to 100% by weight of one or more monovalent olefinically unsaturated alcohols having 10 to 22 carbon atoms per molecule and
    b2.2) 0 to 100% by weight of one or more other monovalent or polyvalent alcohols having a molecular weight of 32 to 4000, provided that the total quantity of the alcohols b2.2) is at most 20% by weight, based on the total weight of component b), at an equivalent ratio of isocyanate groups of component a) to carboxyl groups and hydroxyl groups of component b) of 4:1 to 40:1, and subsequently removing by distillation excess, distillable starting isocyanates a1) and/or a2) from the reaction products until the amount of such isocyanates is at most 0.5% by weight.

The invention also relates to the olefinically unsaturated isocyanates obtained by this process and their use as binders for one-component coating compositions which may be cured at room temperature.

DETAILED DESCRIPTION OF THE INVENTION

The reaction of organic carboxylic acids with excess quantities of organic diisocyanates has been disclosed in DE-AS 1 230 778. However, the products of the process specifically described in this prior publication are acylated urea polyisocyanates which may be used for the usual purposes of polyurethane chemistry. The preparation of olefinically unsaturated isocyanates containing amide groups, such as those obtained according to the present invention, is not described in this prior publication, nor is their use as the binder for coating one-component coating compositions.

The process according to the invention is based on the unexpected finding that when isophorone diisocyanate or mixtures containing isophorone diisocyanate are used as reactants for carboxylic acids, few, if any, products containing acylurea groups are produced, in contrast to the teaching of DE-AS 1 230 778. The products obtained by the process according to the invention are, to the contrary, compounds containing mainly amide groups, as can be demonstrated, for example, by NMR spectroscopy. The products according to the invention are substantially free from acylurea, are crystallization stable and have a low viscosity. One important advantage of the products according to the invention is their rapid drying times when these products are used as lacquer binders. This is attributable to the balanced ratio of isocyanate groups, amide groups and double bonds which are capable of oxidative cross-linking.

The products according to the invention have an isocyanate content of 4 to 20% by weight, preferably 6 to 13% by weight; an iodine number of 20 to 250, preferably 30 to 150; and contain less than 0.5% by weight, preferably less than 0.2% by weight, of distillable starting isocyanates. Their viscosity at 23° C. is generally less than 30,000 mPa.s when solvent free.

Isocyanate component a) is selected from a1) isophorone diisocyanate or mixtures of isophorone diisocyanate with a2) other organic polyisocyanates which are present in quantities of up to 60% by weight, preferably up to 40% by weight and more preferably up to 30% by weight, based on the total weight of component a).

Starting isocyanates a2) have an isocyanate content of 10 to 60% by weight and include aliphatic and cycloaliphatic diisocyanates such as 1,4-diisocyanatobutane, 1,5-diisocyanatopentane, 1,6-diisocyanatohexane (HDI), dodecamethylene diisocyanate, undecane diisocyanate, 2,2,4-trimethylhexane diisocyanate, 1,3-cyclopentylene diisocyanate, cyclohexane-1, 3- and 1,4-diisocyanate, the isomeric diisocyanato dicyclohexylmethanes, 2,5- and 2,6-bis(isocyanatomethyl)bicyclo-[2.2.1]-heptane, isocyanatomethyl-1-methylcyclohexyl-isocyanate (IMCI), 1,4- and 1,3-di(isocyanatoisopropyl)-cyclohexane and xylylene diisocyanate; diisocyanates containing aromatically bound isocyanate groups such as 2,4-diisocyanatotoluene and/or 2,6-diisocyanatotoluene, the isomeric diisoocyanatodiphenylmethanes and higher homologues, 1,3-phenylene diisocyanate, 1,4-phenylene diisocyanate, 4,4'-biphenylene diisocyanate, 1,5-naphthylene diisocyanate, 1,4-naphthylene diisocyanate and 4,4'-diisocyanatodiphenylether; and mixtures of the preceding isocyanates.

Starting isocyanates a2) also include modification products of the above-mentioned diisocyanates containing biuret, uretdione, isocyanurate, allophanate and/or carbodiimide groups. Monofunctional isocyanates may also be used to obtain special properties, but are not preferred.

A mixture of 70 to 100% by weight of isophorone diisocyanate with 0 to 30% by weight of 1,6-diisocyanatohexane is particularly preferred as isocyanate component a).

Reactive component b) has an average functionality in isocyanate addition reactions of 1 to 1.5, preferably 1, and an iodine number of above 90, preferably from 100 to 400. Reactive component b) contains 1 to 100% by weight, preferably 80 to 100% by weight, most preferably 100% by weight, of a carboxylic acid component b1), the remainder being alcohol component b2).

Carboxylic acid component b1) contains of 80 to 100% by weight, preferably 100% by weight, of olefinically unsaturated monocarboxylic acids b1.1), the remainder containing other mono- or polycarboxylic acids b1.2).

Alcohol component b2) contains 0 to 100% by weight, preferably 80 to 100% by weight, of monohydric olefinically unsaturated alcohols b2.1) with the remainder composed of other monohydric or polyhydric alcohols b2.2). The total quantity of alcohol component b2.2), based on the total weight of component b), is at most 20% by weight, preferably not more than 10% by weight.

The carboxylic acids b1.1) may be olefinically unsaturated monocarboxylic acids having an average of 10 to 22, preferably 14 to 20 carbon atoms per molecule and an iodine number above 70, preferably above 90 and most preferably from 100 to 400. Monocarboxylic acids and mixtures thereof derived from the corresponding unsaturated synthetic or natural fatty acids are particularly suitable. Examples include the isomeric decene acids, dodecene acids, tetradecene acids, hexadecene acids, octadecene acids, eicosenic acids, docosenic acids, tetracosenic acids, ximenic acids, 12-oxy-octadecene acids, octadecadiene acids, octadecatriene acids, ecosatetraenic acids, docosapentaenic acids and ricinoleic acid. Examples of naturally occurring fatty acid mixtures include those derived from castor oil, ground nut oil, cotton seed oil, safflower oil, wood oil, soya bean oil, sunflower oil, linseed oil, rape seed oil, tall oil, sperm oil and herring oil. It is also possible, but not preferred, to use olefinically unsaturated hydroxycarboxylic acids as component (b1.1).

When such hydroxycarboxylic acids are used, they fulfil the double function of an unsaturated carboxylic acid b1.1) and an unsaturated alcohol b2.1). This must therefore be taken into account when calculating the quantitative and equivalent ratios of the individual components of component b).

Optional carboxylic acids b1.2) are carboxylic acids having a molecular weight of 46 to 600, preferably 60 to 300. Both monobasic and polybasic carboxylic acids may be used. Examples include formic acid, acetic acid, the isomeric propanoic acids, butanoic acids, pentanoic acids, hexanoic acids, heptanoic acids, octanoic acids, nonanoic acids, decanoic acids, dodecanoic acids, tetradecanoic acids, hexadecanoic acids, octadecanoic acids, eicosanoic acids, docosanoic acids, tetracosanoic acids, dicarboxylic acids such as maleic acid, fumaric acid, malonic acid, adipic acid, sebacic acid, dimeric products of the unsaturated fatty acids b1), tricarboxylic acids [such as trimellitic acid, citric acid and trimeric products of the unsaturated fatty acids b1)], tetracarboxylic acids such as benzene tetracarboxylic acid, and mixtures of the preceding carboxylic acids.

Suitable alcohols b2.1) include olefinically unsaturated alcohols and mixtures of olefinically unsaturated alcohols having an average of 10 to 22, preferably 14 to 20 carbon atoms per molecule and iodine numbers above 70, preferably above 90 and most preferably from 100 to 400. Examples include the monohydric alcohols and alcohol mixtures derived from the corresponding unsaturated synthetic or natural fatty acids or fatty acid mixtures, including the alcohols obtained by reduction of the unsaturated carboxylic acids previously mentioned under b1.1).

Optional alcohols b2.2) have a molecular weight of 32 to 4000, preferably 74 to 286. They may be saturated, monohydric alcohols or polyhydric alcohols. Examples include methanol, ethanol, n-propanol, isopropanol, the isomeric butanols, pentanols and hexanols, n-octanol, n-dodecanol, n-octadecanol, saturated fatty alcohols and polyhydric alcohols such as ethylene glycol, propylene glycol, the isomeric butanediols, hexanediols and octane-diols, glycerol, trimethylolpropane and polymeric polyols such as polyetherpolycarbonate polyols or polyacrylate polyols have the required molecular weights. Mixtures of these alcohols may also be used. The carboxylic acids b1.2) and the alcohols b2.2) are used, if at all, in such quantities within the above-mentioned ranges that the above-mentioned conditions concerning the functionality and iodine number of component b) are fulfilled.

To carry out the process according to the invention, components a) and b) are reacted together in quantities corresponding to an equivalent ratio of isocyanate groups of component a) to carboxyl groups and hydroxyl groups of component b) of 4:1 to 40:1, preferably 5:1 to 20:1 and more preferably 6:1 to 15:1. The reaction is generally carried out at a temperature of 80° to 200° C., preferably 100° to 170° C. The reaction may be accelerated by known catalysts such as triethylamine, tributylamine, N,N,N',N'-tetramethylbutyl-1,4-diamine, bis(dimethylamino)ethyl ether, dimethylethanolamine, 1,4-diazabicyclo-[2.2.2]-octane, diazabicycloundecene, N,N-dimethylbenzylamine, 1- and 2-methylimidazole, tris(dimethylaminomethyl)phenol, pyridine, Mannich bases, morpholines, tetraalkylammonium hydroxides and alkali metal hydroxides such as sodium hydroxide, alkali metal phenolates, metal salts such as iron-(III) chloride or potassium octoate, tin compounds (such as tin-(II)-octoate, tin-(II)-ethylhexanoate, tin-(II)-laurate, aluminium-tri(ethylacetoacetate), dibutyl tin oxide, dibutyl tin dichloride, dibutyl tin diacetate, dibutyl tin dilaurate, dibutyl tin maleate or dioctyl tin diacetate) and mineral acids (such as sulphuric acid, hydrochloric acid, phosphoric acid and perchloric acid).

When alcohols b2) are used, it may be useful to initially react them with the isocyanate component at a temperature of 30° to 100° C. to produce a preliminary product which is subsequently reacted with carboxylic acid component b1).

After the reaction, the excess distillable starting diisocyanate is removed by distillation, preferably by thin layer distillation, down to a content in the final product of less than 0.5% by weight, preferably less than 0.2% by weight.

The products according to the invention are valuable binders for coating compositions which can be cured by atmospheric moisture and atmospheric oxygen.

Before the products according to the invention are used, known catalysts which accelerate oxidative cross-linking may be added. Suitable catalysts are disclosed, for example, in Ullmann, Enzyklopädie der technischen Chemie, 4th Edition, Volume 23, page 42 (Trockenstoffe) Verlag Chemie 1983 and in Offenlegungsschrift DE 4 032 546 and in the literature cited therein. Examples include cobalt, lead, magnesium, zirconium, aluminium, manganese, calcium, cerium, copper, nickel, vanadium, barium and zinc siccatives and mixtures thereof.

These catalysts for accelerating the isocyanate addition reaction may be added to the products according to the invention before they are used in accordance with the invention.

In order to obtain coating compositions having a special profile of properties, it may be advisable to include, as additional binder components, other non-functional polymers or isocyanate functional additives and polymer components which are capable of oxidative cross-linking. Such additional binder components are generally used in a quantity of at most 30% by weight, preferably at most 10% by weight. It is particularly preferred not to add additional binder components for the use of the products according to the invention.

The additional binder components include the alkyl resins disclosed, e.g., in Römpps Chemielexikon, Volume 1, page 202, Frankh's Verlagsbuchhandlung, Stuttgart, 1966; or D. H. Solomon, The Chemistry of Organic Filmformers, pages 75 to 101, John Wiley/Sons Inc., New York 1967. Isocyanate functional binder components which may be used in addition to the products according to the invention include the known lacquer polyisocyanates, i.e., preferably derivatives of aliphatic diisocyanates containing (i) urethane groups, (ii) isocyanurate and/or uretdione groups or (iii) biuret groups, in particular the derivatives of 1,6-diisocyanatohexane.

Other additives may also be used in the coating compositions in addition to the products according to the invention and the other optional binder components. These other additives include solvents; however, these should only be used in small quantities so that the solids content of the coating compositions is above 85% by weight, preferably above 90% by weight. Preferably solvents are not used. Suitable solvents include toluene, xylene, cyclohexane, chlorobenzene, butyl acetate, ethyl acetate, ethyl glycol acetate, pentyl acetate, hexyl acetate, methoxypropyl acetate, tetrahydrofuran, dioxane, acetone, methyl ethyl ketone, xylene, mineral spirits, higher aromatic compounds such as Solvesso or Shellsol solvents and mixtures of the preceding solvents. Relatively odorless isoparaffinic solvents, such as Isopar and Nappar solvents, are particularly suitable. The products according to the invention are readily compatible and miscible with these apolar solvents.

The coating compositions according to the invention may also contain known wetting agents, levelling agents, anti-skinning agents, anti-foamants, matting agents such as silica, aluminium silicates, high boiling waxes, viscosity regulators, pigments, dyes, UV absorbents and stabilizers against thermal or oxidative degradation.

The coating compositions containing the products according to the invention as binders may be used for coating any substrates such as wood, plastics, leather, paper, textiles, glass, ceramics, plaster, brickwork, metals or concrete. They may be applied by known methods such as spraying, brush coating, flooding, casting, immersion or roller application. The coating compositions may be used in the form of clear lacquers or as pigmented lacquers.

The resulting coatings generally harden within a period of 2 to 24 hours at 20° C. to form high quality coatings. They also may be hardened at lower temperatures (down to −5° C.) or accelerated hardening may be carried out at elevated temperatures (for example up to 130° C.).

In the following examples all parts and percentages are by weight, unless otherwise indicated.

EXAMPLES

Examples 1 to 3: (Production and properties of the products according to the invention)

x equivalents of the isocyanate component were introduced into a stirrer apparatus which had been flushed with nitrogen and y equivalents of the dehydrated carboxylic acid component were added dropwise at 150° C. within 3 to 4 hours. After a reaction time of 6 to 7 hours under a nitrogen atmosphere, the mixture was left to cool. The excess diisocyanate was then removed by thin layer distillation under a high vacuum (0.1 to 0.3 mbar) at a temperature of 150° C. Details concerning their preparation and the properties of the resulting products are set forth in Table 1.

TABLE 1

| No. | Isocyanate x (equiv) | Carboxylic acid y (equiv) | NCO % | Viscosity mPa · s | Free diisocyanate % |
|---|---|---|---|---|---|
| 1 | 6.5 IPDI 3.5 HDI | 1 sunflower oil fatty acid | 11.8 | 1000 | 0.12 0.03 |
| 2[1)] | 10 IPDI | 1 safflower oil fatty acid | 9.65 | 3000 | 0.19 |
| 3[1)] | 10 IPDI | 1 soya bean oil fatty acid | 9.74 | 3200 | 0.12 |

[1)]According to $^{13}C$—NMR spectroscopic analysis, about 75 equivalent % of the groups containing carbonyl groups in the products of the process were amide groups.

Comparison Examples 4 to 7 (Production and properties of comparison products)

Comparison products were prepared following the procedure described for Examples 1–3. Details concerning their preparation and the properties of the resulting products are set forth in Table 2.

TABLE 2

| No. | Iso-cyanate x (equiv) | Carboxylic Acid y (equiv) | NCO % | Viscosity mPa · s | Free diiso-cyanate % |
|---|---|---|---|---|---|
| 4 | 10 HDI | 1 Sunflower oil fatty acid | — | crystal-line | — |
| 5 | 10 HDI | 1 Soya bean oil fatty acid | — | crystal-line | — |
| 6 | 2 IPDI 8 HDI | 1 Soya bean oil fatty acid | 12.5 | partly crystal-line | 0.18 0.03 |
| 7* | 1 IPDI | 1 Soya bean oil fatty acid | <1 | 92000 | — |

*Product not thin layer distilled

Examples 8 to 10 (Production and properties of clear coatings according to the invention)

The clear coating compositions had the following composition:
93.4 parts of lacquer binder
2.8 parts of Octa Soligen Calcium 4
0.5 part of Octa Soligen Cobalt 6
2.8 parts of Octa Soligen Zirconium 18
0.5 parts of Ascinin R conc. (commercial anti-skinning agent available from H. C. Starck, Ooslar, Germany).
The Octa Soligen siccatives are available from Borchers AG, Germany.

The binder formulations set forth in Table 3 were applied to clean glass plates in a layer thickness of 120 μm and hardened at room temperature. The resulting drying times (hour to attain sand dry at 20° C.), resistance to pressure (according to DIN 53 150), values for pendulum damping (according to DIN 53 157) and solvent resistance (0=unchanged, 5=dissolved) are set forth in Table 3.

TABLE 3

| No. | Binder from Example | Hours to attain sand dry | Hours to attain pressure resistance | Pendulum damping after 7d in sec | Solvent resistance |
|---|---|---|---|---|---|
| 8 | 1 | 3 | >8 <18 | 75 | 1–2 |
| 9 | 2 | 2.5 | >8 <18 | 112 | 1–2 |
| 10 | 3 | 4.5 | >8 <18 | 110 | 1–2 |

Comparison Examples 11 and 12 (not according to the invention)

Coating compositions were prepared with the binders from comparison Examples 6 and 7 using the same formulation set forth above for Examples 8 to 10. The properties of the resulting coatings are set forth in Table 4.

TABLE 4

| No. | Binder from Comparison Example | Hours to attain sand dry | Hours to attain pressure resistance | Pendulum damping after 7 days in sec |
|---|---|---|---|---|
| 11 | 6 | >8 | >30 | 80 |
| 12 | 7 | >8 | >30 | 63 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an olefinically unsaturated isocyanate predominantly containing amide groups as opposed to acylated urea groups and having an isocyanate content of 4 to 20% by weight which comprises reacting
   a) an isocyanate component having an isocyanate content of 20 to 51% by weight and an (average) functionality of less than 2.5 and containing
      a1) 40 to 100% by weight of isophorone diisocyanate and
      a2) 0 to 60% by weight of one or more other organic polyisocyanates having an isocyanate content of 10 to 60% by weight with
   b) an olefinically unsaturated reactive component having an average functionality in isocyanate addition reactions of less than 1.5 and an iodine number above 70, and containing
      b1) 1 to 100% by weight of a carboxylic acid component containing
         b1.1) 80 to 100% by weight of one or more monobasic, olefinically unsaturated carboxylic acids having 10 to 22 carbon atoms per molecule and
         b1.2) 0 to 20% by weight of one or more other monobasic or polybasic carboxylic acids having a molecular weight of 46 to 350 and
      b2) 0 to 99% by weight of an alcohol component containing
         b2.1) 0 to 100% by weight of one or more monovalent olefinically unsaturated alcohols having 10 to 22 carbon atoms per molecule and
         b2.2) 0 to 100% by weight of one or more other monovalent or polyvalent alcohols having a molecular weight of 32 to 4000, provided that the total quantity of alcohols b2.2) is at most 20% by weight, based on the total weight of component b),
at an equivalent ratio of isocyanate groups of component a) to carboxyl groups and hydroxyl groups of component b) of 4:1 to 40:1, and subsequently removing by distillation excess, distillable starting isocyanates a1) and/or a2) from the reaction product until the amount of such isocyanates is at most 0.5% by weight.

2. The process of claim 1 wherein component a) contains at least 60% by weight of isophorone diisocyanate.

3. The process of claim 1 wherein component b) contains at least 80% by weight of carboxylic acids b1).

4. The process of claim 2 wherein component b) contains at least 80% by weight of carboxylic acids b1).

5. The process of claim 1 wherein component b) contains 100% of unsaturated carboxylic acids b1.1).

6. The process of claim 2 wherein component b) contains 100% of unsaturated carboxylic acids b1.1).

7. An olefinically unsaturated isocyanate predominantly containing amide groups as opposed to acylated urea, groups and having an isocyanate content of 4 to 20% by weight which is prepared by a process which comprises reacting
   a) an isocyanate component having an isocyanate content of 20 to 51% by weight and an (average) functionality of less than 2.5 and containing
      a1) 40 to 100% by weight of isophorone diisocyanate and
      a2) 0 to 60% by weight of one or more other organic polyisocyanates having an isocyanate content of 10 to 60% by weight with
   b) an olefinically unsaturated reactive component having an average functionality in isocyanate addition reactions of less than 1.5 and an iodine number above 70, and containing b1) 1 to 100% by weight of a carboxylic acid component containing
  b1.1) 80 to 100% by weight of one or more monobasic, olefinically unsaturated carboxylic acids having 10 to 22 carbon atoms per molecule and
  b1.2) 0 to 20% by weight of one or more other monobasic or polybasic carboxylic acids having a molecular weight of 46 to 350 and
b2) 0 to 99% by weight of an alcohol component containing
  b2.1) 0 to 100% by weight of one or more monovalent olefinically unsaturated alcohol having 10 to 22 carbon atoms per molecule and
  b2.2) 0 to 100% by weight of one or more other monovalent or polyvalent alcohols having a molecular weight of 32 to 4000, provided that the total quantity of the alcohols b2.2) is at most 20% by weight, based on the total weight of component b), at an equivalent ratio of isocyanate groups of component a) to carboxyl groups and hydroxyl groups of component b) of 4:1 to 40:1, and subsequently removing by distillation excess, distillable starting isocyanates a1) and/or a2) from the reaction product until the amount of such isocyanates is at most 0.5% by weight.

8. The isocyanate of claim 7 wherein component a) contains at least 60% by weight of isophorone diisocyanate.

9. The isocyanate of claim 7 wherein component b) contains at least 80% by weight of carboxylic acids b1).

10. The isocyanate of claim 8 wherein component b) contains at least 80% by weight of carboxylic acids b1).

11. The isocyanate of claim 7 wherein component b) contains 100% of unsaturated carboxylic acids b1.1).

12. The isocyanate of claim 8 wherein component b) contains 100% of unsaturated carboxylic acids b1.1).

13. A one-component coating composition, which may be cured at room temperature, wherein the binder contains the olefinically unsaturated isocyanate of claim 7.

* * * * *